United States Patent [19]

Anderson et al.

[11] Patent Number: 4,656,163

[45] Date of Patent: Apr. 7, 1987

[54] COMPOSITIONS AND METHODS OF COMBATING PESTS EMPLOYING SULPHENIC ACID AMIDES IN COMBINATION WITH KNOWN NEMATICIDES OR INSECTICIDES

[75] Inventors: John Anderson; Bernhard Homeyer, both of Leverkusen; Engelbert Kühle, Bergisch-Gladbach; Hans Scheinpflug, Leverkusen, all of Fed. Rep. of Germany; Walter M. Zeck; Donald E. Simonet, both of Vero Beach, Fla.

[73] Assignees: Bayer Aktiengesellschaft, Leverkusen, Fed. Rep. of Germany; Mobay Corporation, Pittsburgh, Pa.

[21] Appl. No.: 798,216

[22] Filed: Nov. 14, 1985

Related U.S. Application Data

[62] Division of Ser. No. 701,476, Feb. 14, 1985, Pat. No. 4,603,214.

[51] Int. Cl.[4] .................... A01N 37/02; A01N 37/10; A01N 37/12; A01N 37/34; A01N 37/44; A01N 43/08; A01N 47/10; A01N 53/00; A01N 55/02; A01N 57/00; A01N 57/10; A01N 57/18

[52] U.S. Cl. ........................................ 514/84; 514/86; 514/89; 514/90; 514/112; 514/124; 514/127; 514/128; 514/137; 514/141; 514/144; 514/147; 514/469; 514/470; 514/477; 514/479; 514/490; 514/492; 514/494; 514/500; 514/501; 514/502; 514/520; 514/521; 514/523; 514/531; 514/532; 514/534; 514/537; 514/546

[58] Field of Search ................. 514/84, 89, 90, 112, 514/124, 127, 128, 137, 141, 144, 147, 469, 470, 477, 479, 490, 492, 494, 500, 501, 502, 520, 521, 523, 531, 532, 534, 537, 546

[56] References Cited

U.S. PATENT DOCUMENTS

| | | | |
|---|---|---|---|
| 3,636,076 | 1/1972 | Kuhle et al. | 560/18 |
| 3,647,836 | 3/1972 | Paterson | 260/429.9 X |
| 3,894,078 | 7/1975 | Fridinger | 260/429.9 X |
| 3,939,189 | 2/1976 | Kuhle et al. | 260/429.9 |
| 4,156,737 | 5/1979 | Bertelli | 260/438.1 X |

OTHER PUBLICATIONS

C.A., 81, 91222k (1974).

*Primary Examiner*—Allen J. Robinson
*Attorney, Agent, or Firm*—Sprung Horn Kramer & Woods

[57] ABSTRACT

The present invention relates to the use of the sulphenic acid amides of the general formula (I)

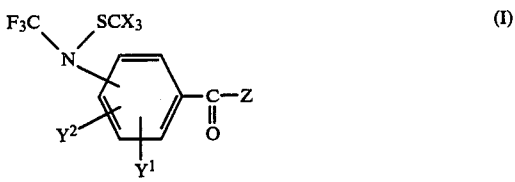

in which
X represents identical or different halogen atoms,
$Y^1$ and $Y^2$ are identical or different and represent hydrogen, halogen, alkyl, alkoxy, halogenoalkyl or $NO_2$ and
Z represents halogen, —OH, —NHOH or the group —$OR^1$,
in which
$R^1$ denotes optionally substituted radicals from the series comprising alkyl, alkenyl, alkinyl, cycloalkyl, aryl, aralkyl and heterocyclyl, or
Z represents the group

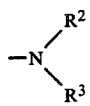

in which
$R^2$ and $R^3$ are identical or different and denote hydrogen or a heterocyclic radical, or
Z represents the group —OM in which M denotes ammonium or the equivalent of an alkali metal, alkaline earth metal or heavy metal cation, for prolonging the duration of a high activity in agents for combating soil pests.

6 Claims, No Drawings

COMPOSITIONS AND METHODS OF COMBATING PESTS EMPLOYING SULPHENIC ACID AMIDES IN COMBINATION WITH KNOWN NEMATICIDES OR INSECTICIDES

This is a division, of application Ser. No. 701,476, filed Feb. 14, 1985, now U.s. Pat. No. 4,603,214.

The present invention relates to new agents for combating pests which can preferably be used in plant protection for combating nematodes and arthropods, in particular insects. The new agents for combating pests contain at least one suitable active compound from the series comprising carbamates, P esters (phosphoric acid esters and phosphonic acid esters, including the ester-amides and the particular thiono, thiol and thiono-thiol derivatives) and pyrethroids, and at least one suitable sulphenic acid amide. The new agents for combating pests are distinguished by a particularly long-lasting activity when used as nematicides and soil insecticides.

The combating of nematodes and soil insects is gaining ever more importance in intensive cultivation of crop plants. Insects which continuously or at times, for example during certain development stages, live in or on the soil or close to the soil, for example on parts of plants, are designated soil insects (compare also B. Homeyer in Chemie der Pflanzenschutz- und Schädlingsbekäampfungsmittel [Chemistry of the Plant Protection Agents and Agents for Combating Pests], published by R. Wegler, Volume 1, Springer-Verlag, Berlin 1970, pages 464 to 474). Such pests should preferably be combated preventively, so that an agent for combating soil pests must be applied early and must have a reliable and adequate activity for the maximum possible period. It is frequently advantageous for the agents for combating pests already to be applied during sowing, in order to simultaneously achieve protection of the seed and of the developing yound plants.

Since the soil treatment agents currently available do not always reliably display an adequately long activity under adverse weather and/or soil conditions, it is an object of the invention to provide new agents for combating pests which allow long-lasting protection of the plants, even under adverse conditions.

It has now been found that agents for combating pests which contain at least one substance, which is active against nematodes and/or insects, especially soil insects, e.g., carbamates, P esters and pyrethroids, (called the "active compound" below) and at least one sulphenic acid amide of the general formula (I)

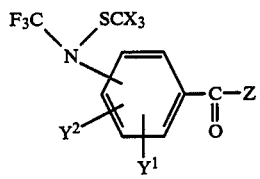

in which
X represents identical or different halogen atoms,
Y¹ and Y² are identical or different and represent hydrogen, halogen, alkyl, alkoxy, halogenoalkyl or NO₂ and
Z represents halogen, —OH, —NHOH or the group —OR¹,
in which
R¹ denotes optionally substituted radicals from the series comprising alkyl, alkenyl, alkinyl, cycloalkyl, aryl, aralkyl and heterocyclyl, or
Z represents the group

in which
R² and R³ are identical or different and denote hydrogen or optionally substituted radicals from the series comprising alkyl, aryl and a heterocyclic radical, or
Z represents the group —OM,
in which M denotes ammonium or the equivalent of an alkali metal, alkaline earth metal or heavy metal cation, have a particularly long-lasting high activity against nematodes or soil insects. The sulphenic acid amides of the general formula (I) are hereinbelow sometimes identified as "action prolongers" or "extenders".

The duration of action of the new pesticidal compositions is considerably longer than the duration of action of the active compounds. Since the sulphenic acid amides of the general formula (I) have virtually no nematicidal or soil-insecticidal activity at the concentrations employed, the occurrence of the prolonging of the action must be regarded as decidedly unexpected and surprising.

Preferred active compounds for the new agents for combating pests are carbamates, P esters (including the ester-amides and the thiono, thiol and thionothiol derivatives) and pyrethroids which are usually employed as agents for combating soil pests (compare Chemistry of Festicides, edited by K. H. Buchel, John Wiley & Sons, New York, 1983, Farm Chemicals Handbook, Meister Publishing Co., Wolloughby, 1983, U.S. Pat. No. 4,127,652 and European Patent Application 84 105 133.7 and corresponding U.S. patent application Ser. No. 06/606, 106).

The active compounds described below are preferred as the P esters, carbamates and pyrethroids:

(A) P esters of the general formula (II)

in which
Q represents oxygen or sulphur,
U, V and W are identical or different and represent oxygen or sulphur, it moreover also being possible for one of the radicals U, V and W to denote a direct bond or the —NH— group,
R⁴ and R⁵ are identical or different and represent C₁-C₄-alkyl (preferably C₁-C₃-alkyl) and R⁶ represents $C_1$-$C_5$-alkyl (preferably $C_1$-$C_2$-alkyl), which can be substituted by $C_1$-$C_4$-alkylthio (preferably $C_1$-$C_2$-alkylthio) and/or halogen (preferably chlorine), or represents $C_2$-$C_4$-alkenyl, which can be substituted by halogen (preferably chlorine) and/or halogenophenyl (preferably chlorophenyl) or represents phenyl, which can be substituted by halogen (preferably chlorine and/or bromine), $C_1$-$C_4$-alkyl (preferably methyl), $C_1$-$C_4$-alkylthio (preferably methylthio), $C_1$-$C_4$-alkylsulphinyl (preferably methylsulphinyl) and/or $C_1$-$C_4$-alkoxycarbonyl (preferably propoxycarbonyl), or represents pyridyl, which can be substituted by halogen (preferably chlorine) or represents pyrimidinyl, which can be substituted by $C_1$-$C_4$-alkyl, $C_3$-$C_6$-cycloalkyl and/or phenyl, or represents the radical 5-chloro-1-(1-methylethyl)-1H-1,2,4-triazol-3-yl, or represents the group —N=CR⁷ (CN), wherein R⁷ denotes phenyl which is optionally substituted by halogen (preferably chlorine).

In formula II, R⁴ and R⁵ preferably represent methyl, ethyl or n- and i-propyl.

R⁶ preferably represents chloromethyl, propyl, ethylthiomethyl, ethylthioethyl, t-butylthiomethyl, 1-(2,4-dichlorophenyl)-2-chloro-ethen-1-yl, phenyl, 3-methyl-4-methylthio-phenyl, 4-methylsulphinyl-phenyl, 2-i-propoxycarbonylphenyl, 2,4-dichlorophenyl, 2,4,5-trichlorophenyl, 2,5-dichloro-4-bromophenyl, 3,5,6-trichloro-2-pyridyl, the radical —N=(CN)(phenyl) or the radical 5-chloro-1-(1-methylethyl)-1-H-1,2,4-triazol-3-yl.

The following P esters may be mentioned as examples (common name or chemical name): disulfoton, femamiphos, isofenfos, trichloronat, fensulfothion, protiofos, phoxim, chlorfenvinfos, bromophos, terbufos, chloropyrifos, chlormephos, fenofos, isazophos, ethoprofos, phorate, 0-ethyl 0-i-propyl 0-(2-t-butyl-pyrimidin-5-yl) thionophosphate and 0,0-diethyl 0-(2-t-butyl-pyrimidin-5-yl)thionophosphate. Preferred esters which may be mentioned are: terbufos, chlorpyrifos, fenofos, isofenfos, fenaminphos, phorate, 0-ethyl 0-i-propyl 0-(2-t-butylpyrimidin-5-yl)thionophosphate and 0,0-diethyl 0-(2-t-butyl-pyrimidin-5-yl)thionophosphate.

(B) Carbamates of the general formula (III)

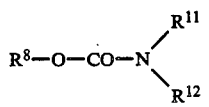
(III)

in which R⁸ represents phenyl, which can be substituted by $C_1$-$C_4$-alkylthio-$C_1$-$C_4$-alkyl (preferably ethylthiomethyl), $C_1$-$C_4$-alkyl (preferably methyl), $C_1$-$C_4$-alkoxy and/or $C_1$-$C_4$-alkylthio (preferably methylthio), or represents the radical 2,3-dihydro-2,2-dimethyl-7-benzofuranyl, or represents the radical —N=CR⁹R¹⁰, in which R⁹ denotes $C_1$-$C_4$-alkyl (preferably propyl), which can be substituted by $C_1$-$C_4$-alkylthio (preferably methylthio), or R⁹ denotes the radical CON ($C_1$-$C_4$-alkyl)₂ preferably CONH($CH_3$)₂) and R¹⁰ denotes hydrogen or $C_1$-$C_4$-alkylthio (preferably methylthio), R¹¹ represents $C_1$-$C_4$-alkyl (preferably methyl) and R¹² denotes hydrogen or the radical —S—NR¹³R¹⁴, in which R¹³ denotes $C_1$-$C_4$-alkyl and R¹⁴ denotes COOC₁-$C_4$-alkyl (preferably n-butyl) or $C_1$-$C_4$-alkyl, which can be substituted by COOC₁-$C_4$-alkyl (preferably COOC₂H₅), R⁸ preferably represents 3,4,5-trimethylphenyl, 2-ethylthiomethylphenyl, 3,5-dimethyl-4-methylthophenyl, 2,3-dihydro-2,2-dimethyl-7-benzofuranyl, —N=CH—C(CH₃)₂(SCH₃), —N=C(SCH₃)(CON(CH₃)₂) or 2-i-propoxyphenyl, R¹¹ preferably represents methyl.

R¹² preferably represents hydrogen, —S—N(CH₃)(COOC₄H₉n), —S—N(C₄H₉n)₂ or —S—N(iC₃H₇)(CH₂CH₂COOC₂H₅).

The following carbamates may be mentioned as examples (common name or chemical name): ethiofencarb, carbofuran, methiocarb, furatiocarb, carbosulfan, aminosulfuram, aldicarb, oxamyl and 3,4,5-trimethylphenyl carbamate. Carbamates which may be mentioned as preferred are: carbofuran, furatiocarb, carbosulfan, aminosulfuram and aldicarb.

(C) Pyrethroids of the general formula (IV)

(IV)

in which R¹⁵ represents the group

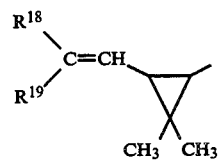

in which

R¹⁸ denotes halogen (preferably chlorine or bromine) or $C_1$-$C_4$-alkyl (preferably methyl) and R¹⁹ denotes halogen (preferably chlorine or bromine), $C_1$-$C_4$-alkyl (preferably methyl) or phenyl, which can be substituted by halogen (preferably chlorine), or R¹⁵ represents the group

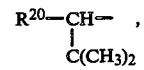

in which

R²⁰ denotes phenyl, which can be substituted by halogen (preferably chlorine), $C_1$-$C_4$-halogenoalkyl (halogen is preferably chlorine or fluorine), $C_1$-$C_4$-halogenoalkoxy (halogen is preferably chlorine or fluorine) and/or $C_1$-$C_4$-alkoxy, R¹⁶ represents hydrogen or cyano and R¹⁷ represents phenyl, which can be substituted by halogen (preferably fluorine or chlorine) and/or phenoxy.

R¹⁸ and R¹⁹ in the groups R¹⁵ preferably represent chlorine, bromine or methyl, or R¹⁸ represents chlorine and R¹⁹ represents 4-chlorophenyl. R²⁰ preferably represents 4-chlorophenyl or 2-chloro-4-trifluoromethylphenyl.

$R^{17}$ preferably represents pentafluorophenyl, 3-phenoxyphenyl or 4-fluoro-3-phenoxyphenyl.

Examples of pyrethroids which may be mentioned are (common name): phenothrin, permethrin, decamethrin, fenvalerat, fluvalinate, cyfluthrine and fenfluthrin.

The present invention thus relates to the new use of the sulphenic acid amides of the general formula (I) as agents for prolonging the action of nematicidal and insecticidal carbamates, P esters and pyrethroids, agents for combating pests containing at least one compound of the formula (I) and at least one nematicidal or insecticidal active compound from the series comprising the carbamates, P esters and pyrethroids, and the use of these agents for combating pests for combating soil pests, preferably nematodes and insects. For simplicity, the term insects will in each case also include the less important arthropods which occur as soil pests, for example ants, springtails, millepedes, termites, woodlice and root mites.

The present invention also relates to the new sulphenic acid amides of the general formula (I) in which X, $Y^1$ and $Y^2$ have the abovementioned meaning and Z represents the group —OM, M denoting ammonium or the equivalent of an alkali metal, alkaline earth metal or heavy metal cation, and to a process for the preparation of these salts.

The present invention also relates to the new sulphenic acid amides of the general formula (I) in which X, $Y^1$ and $Y^2$ have the abovementioned meanings and Z represents the group $OR^1$, in which $R^1$ denotes alkyl, alkenyl or alkinyl which is optionally substituted by halogen, cyano, alkylthio, alkoxy or alkoxyalkoxy, and to a process for the preparation of these compounds.

The other compounds of the general formula (I) are known or can be obtained by generally known methods (compare, for example, German Patent Application No. A-1,810,580, German Patent Application No. A-1,543,614 (corresponding to U.S. Pat. No. 3,597,480 and U.S. Pat. No. 3,723,628), German Patent Application B-1,293,754 and German Patent Application No. A-1,668,026 (corresponding to U.S. Pat. No. 3,547,992), German Patent Application No. A-1,919,180 (corresponding to U.S. Pat. No. 3,636,076), German Patent Application No. A-2,257,345 and German Patent Application No. A-2,311,983).

The new salts (Z=OM) can be obtained by the generally customary salt formation methods from the acids (Z=—OH) by reaction with ammonia, amines or metal bases, such as hydroxides, carbonates and bicarbonates. The reaction is preferably carried out at 0° to 30° C. in aqueous-alcoholic solution, it being possible to use lower alcohols, such as methanol or ethanol, as solvents.

The reactants are preferably employed in equimolar (or equivalent) amounts. Heavy metal salts can advantageously be obtained from the alkali metal salts in aqueous-alcoholic solutions (methanol or ethanol) by reaction with heavy metal salts (for example the chlorides or sulphates), in which case the heavy metal salts precipitate out of the solution as crystals and can easily be isolated.

The new compounds of the general formula (I) in which
X represents identical or different halogen atoms,
$Y^1$ and $Y^2$ are identical or different and represent hydrogen, halogen, alkyl, alkoxy, halogenoalkyl or $NO_2$ and
Z represents the group $-OR^1$,
in which $R^1$ denotes alkyl, alkenyl or alkinyl which is optionally substituted by halogen, cyano, alkoxy, alkylthio or alkoxyalkoxy, can be obtained by a process in which the compounds of the general formula (V)

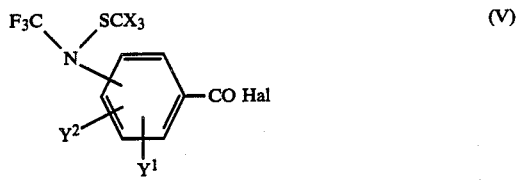

in which X, $Y^1$ and $Y^2$ have the abovementioned meaning and Hal represents halogen (preferably fluorine or chlorine), are reacted with compounds of the general formula (VI)

$$R^1-OH \qquad (VI)$$

in which $R^1$ has the abovementioned meaning, in the presence of an acid-binding agent and in the presence of a solvent.

Possible solvents here are all the inert organic solvents. These include ethers, such as diethyl ether, tetrahydrofuran and dioxane, hydrocarbons, such as benzene, and chlorohydrocarbons, such as chloroform and chlorobenzene.

A tertiary base, such as triethylamine, or inorganic bases, such as alkali metal hydroxides or carbonates, are added to the reaction mixture to bond the hydrogen halide formed during the reaction. It is also possible to use alkali metal alcoholates or phenolates directly as starting materials and to carry out the reaction according to the invention in the aqueous phase.

The reaction temperatures can be varied within a substantial range, and the reaction is in general carried out between 0° and 100° C., preferably between 20° and 60° C. The process is in general carried out with molar amounts. However, in many cases it has proved advantageous to employ a slight excess of the hydroxy compound (about 5–25% by weight).

The reaction mixture is worked up in the customary manner. The compounds according to the invention are either colorless crystals or oils, which, depending on the molecular weight, can frequently be distilled.

In the general formulae (I) and (V), X preferably denotes fluorine or chlorine and $X_3$ preferably represents the radical $ClF_2$ or $Cl_2F$, and especially preferably $Cl_2F$.

Halogen in the definition of $Y^1$, $Y^2$ and Z denotes fluorine, chlorine, bromine or iodine, preferably fluorine, chlorine or bromine, and in the case of $Y^1$ and $Y^2$ particularly preferably chlorine and in the case of Z particularly preferably fluorine.

Alkyl and alkoxy in the definition of $Y^1$ and $Y^2$ preferably contain 1 to 4 carbon atoms, methyl, ethyl and n- and i-propyl and methoxy, ethoxy and n- and i-propoxy being mentioned as examples. Methyl and methoxy are particularly preferred.

Halogenoalkyl $Y^1$ and $Y^2$ preferably contains 1 to 4 carbon atoms and 1 to 5 identical or different halogen atoms (preferably fluorine and chlorine, in particular fluorine), trifluoromethyl, dichlorofluoromethyl and pentafluoroethyl being mentioned as examples.

Alkyl $R^1$ (general formulae I and VI) preferably contains 1 to 12, in particular 1 to 4, carbon atoms, methyl, ethyl and n- and i-propyl being mentioned as examples.

Alkenyl and alkinyl $R^1$ preferably contain 1 double or triple bond and preferably 3 to 4 carbon atoms, allyl and propargyl being mentioned as examples.

Cycloalkyl $R^1$ preferably contains 3 to 7, in particular 5 or 6, carbon atoms. Cyclopentyl and cyclohexyl may be mentioned as examples.

Aryl $R^1$ preferably denotes phenyl or naphthyl, in particular phenyl.

Aralkyl $R^1$ preferably contains 1 to 3 carbon atoms in the alkyl part and 5 or 10 carbon atoms in the aryl part, benzyl and phenethyl being mentioned as examples.

Heterocyclyl $R^1$ is a heterocyclic radical, the ring of which contains 1 or more, preferably 1 to 3, and in particular 1 or 2, identical or different hetero-atoms, such as oxygen, sulphur or nitrogen, and can be aromatic, unsaturated or saturated, and preferably contains 5 or 6 ring members. Examples which may be mentioned are: furyl, thienyl, tetrahydrofuryl, pyranyl, pyrrolyl, imidazolyl and pyridyl.

Alkyl $R^2$ and $R^3$ preferably contains 1 to 6, in particular 1 to 4, carbon atoms, examples which may be mentioned being methyl, ethyl and n- and i-propyl.

Aryl $R^2$ and $R^3$ preferably denotes phenyl.

The heterocyclic radicals $R^2$ and $R^3$ have the meaning given for heterocyclyl $R^1$. In addition $R^2$ and $R^3$ can together with the nitrogen atom to which they are attached form a 5- or 6-membered ring, which can be interrupted by a heteroatom (as nitrogen, oxygen or sulfur).

The radicals mentioned as optionally substituted in the invention of the radicals can carry one or more, preferably 1 to 3, and in particular 1 or 2, identical or different substituents. Examples of substituents which may be mentioned are: alkyl with preferably 1 to 4, in particular 1 or 2, carbon atoms, such as methyl, ethyl, n- and i-propyl and n-, i- and t-butyl; alkoxy with preferably 1 to 4, in particular 1 or 2, carbon atoms, such as methoxy, ethoxy, n- and i-propoxy and n-, i- and t-butoxy; alkylthio with preferably 1 to 4, in particular 1 or 2, carbon atoms, such as methylthio, ethylthio, n- and i-propylthio and n-, i- and t-butylthio; halogenoalkyl with preferably 1 to 4, in particular 1 or 2, carbon atoms and preferably 1 to 5, in particular 1 to 3, halogen atoms, the halogen atoms being identical or different and halogen atoms being preferably fluorine, chlorine or bromine, in particular fluorine, such as trifluoromethyl or trichloromethyl; hydroxyl; halogen, preferably fluorine, chlorine, bromine and iodine, in particular chlorine and fluorine; cyano; nitro; amino; monoalkyl- and dialkyl-amino with preferably 1 to 4, in particular 1 or 2, carbon atoms per alkyl group, such as methylamino, methyl-ethyl-amino, n- and i-propyl-amino and methyl-n-butylamino; carboxyl; carbalkoxy with preferably 2 to 4, in particular 2 or 3, carbon atoms, such as carbomethoxy and carboethoxy; sulpho (—SO$_3$H); alkylsulphonyl with preferably 1 to 4, in particular 1 or 2, carbon atoms, such as methylsulphonyl and ethylsulphonyl; and arylsulphonyl with preferably 6 or 10 aryl carbon atoms, such as phenylsulphonyl.

Ammonium M can represent the NH$_4^+$ ion or the cation of a mono-, di- or tri-alkylamine with preferably 1 to 4, in particular 1 or 2, carbon atoms per alkyl group. Examples which may be mentioned are ammonium, methylammonium and trimethylammonium.

Preferred alkali metal, alkaline earth metal or or heavy metal cations M are the cations of sodium, potassium, calcium, magnesium, copper, zinc, manganese, nickel and iron, particularly preferably of copper and zinc.

Sulphenic acid amides of the general formula (I) which are preferably employed according to the invention are those in which X represents fluorine and chlorine (X$_3$ preferably representing Cl$_2$F or F$_2$Cl), $Y^1$ represents hydrogen, halogen (preferably chlorine), C$_1$-C$_4$-alkyl (preferably methyl), C$_1$-C$_4$-alkoxy (preferably methoxy) or NO$_2$, $Y^2$ represents hydrogen or halogen (preferably chlorine), Z represents halogen (preferably fluorine), —OH or —NHOH, or represents the group —OR$^1$, in which $R^1$ denotes C$_1$-C$_{12}$-alkyl (preferably C$_1$-C$_4$-alkyl) which is optionally substituted by halogen (preferably chlorine), C$_1$-C$_4$-alkoxy (preferably methoxy or ethoxy), C$_1$-C$_4$-alkylthio (preferably C$_1$- or C$_2$-alkylthio), C$_1$-C$_4$-alkoxy-C$_1$-C$_4$-alkoxy (preferably methoxyethoxy) or CN, or $R^1$ denotes C$_2$-C$_4$-alkenyl (preferably allyl) or C$_3$-C$_4$-alkinyl (preferably propargyl), or $R^1$ denotes phenyl which is optionally substituted by halogen (preferably chlorine) or C$_1$-C$_4$-alkoxycarbonyl (preferably methoxycarbonyl), or $R^1$ denotes thienyl which is optionally substituted by C$_1$-C$_4$-alkyl and/or C$_1$-C$_4$-alkoxycarbonyl, or $R^1$ represents the group —NR$^2$R$^3$, in which $R^2$ represents hydrogen and $R^3$ represents hydrogen or C$_1$-C$_4$-alkyl which is optionally substituted by halogen (preferably chlorine), C$_1$-C$_4$-alkoxy (preferably methoxy) or CN, or $R^1$ represents the group —OM, in which M denotes ammonium or one equivalent of an alkali metal (preferably sodium or potassium), an alkaline earth metal (preferably calcium or magnesium) or a heavy metal (preferably copper or zinc).

The novel sulphenic acid amides of the general formula (I) which are moreover preferred according to the invention are those in which X represents fluorine and chlorine (X$_3$ preferably represent Cl$_2$F), Y$^1$ represents hydrogen, C$_1$–C$_4$-alkyl (preferably methyl), C$_1$–C$_4$-alkoxy (preferably methoxy) or chlorine, Y$^2$ represents hydrogen and Z represents the group OR$^1$, in which R$^1$ denotes C$_1$–C$_{12}$-alkyl (preferably C$_1$–C$_4$-alkyl) which can be substituted by halogen (preferably chlorine), C$_1$–C$_4$-alkoxy (preferably methoxy or ethoxy), C$_1$–C$_4$-alkylthio (preferably methylthio or ethylthio) or C$_1$–C$_4$-alkoxy-C$_1$–C$_4$-alkoxy (preferably methoxy-C$_1$–C$_2$-alkoxy), or in which R$^1$ represents allyl or propargyl.

The new copper and zinc salts of the compounds of the general formula (I) are particularly preferred according to the invention, since, because of their solubilities, they can be particularly advantageously formulated.

Some examples of compounds of the general formula (I) which can be particularly advantageously employed according to the invention are listed below:

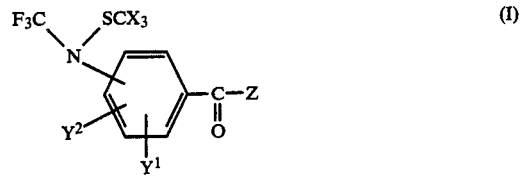

(I)

TABLE 1

| Extender No. | —N(CF$_3$)SCCX$_3$ | Y$^1$ | Y$^2$ | Z |
|---|---|---|---|---|
| 1 | 4-N(CF$_3$)SCCl$_2$F | H | H | OH |
| 2 | 3-N(CF$_3$)SCCl$_2$F | 4-Cl | H | OH |
| 3 | 3-N(CF$_3$)SCClF$_2$ | H | H | OH |
| 4 | 4-N(CF$_3$)SCCl$_2$F | H | H | O½ Cu$^{2+}$ |
| 5 | 4-N(CF$_3$)SCCl$_2$F | H | H | O½ Zn$^{2+}$ |
| 6 | 4-N(CF$_3$)SCCl$_2$F | 3-CH$_3$ | H | OH |
| 7 | 4-N(CF$_3$)SCCl$_2$F | 3-CH$_3$ | H | OH |
| 8 | 3-N(CF$_3$)SCCl$_2$F | 4-CH$_3$ | H | OH |
| 9 | 3-N(CF$_3$)SCCl$_2$F | H | H | ─O─⌬─Cl |
| 10 | 3-N(CF$_3$)SCCl$_2$F | 4-CH$_3$O | H | OH |
| 11 | 3-N(CF$_3$)SCCl$_2$F | 6-Cl | H | OH |
| 12 | 3-N(CF$_3$)SCCl$_2$F | H | H | OH |
| 13 | 3-N(CF$_3$)SCCl$_2$F | H | H | —NHOH |
| 14 | 3-N(CF$_3$)SCCl$_2$F | 4-Cl | 5-NO$_2$ | OH |
| 15 | 3-N(CF$_3$)SCCl$_2$F | 4-Cl | H | OC$_{12}$H$_{25}$ |
| 16 | 4-N(CF$_3$)SCCl$_2$F | H | H | (thiophene with OCH$_3$, COOCH$_3$, COOCH$_3$) |
| 17 | 3-N(CF$_3$)SCCl$_2$F | 4-Cl | H | F |
| 18 | 3-N(CF$_3$)SCCl$_2$F | 4-Cl | H | O½ Cu$^{2+}$ |
| 19 | 3-N(CF$_3$)SCCl$_2$F | 4-Cl | H | O½ Zn$^{2+}$ |
| 20 | 3-N(CF$_3$)SCCl$_2$F | H | H | OCH$_2$CH$_2$Cl |
| 21 | 3-N(CF$_3$)SCCl$_2$F | H | H | OCH$_2$CCl$_3$ |
| 22 | 3-N(CF$_3$)SCCl$_2$F | H | H | OCH$_2$CH$_2$OCH$_3$ |
| 23 | 3-N(CF$_3$)SCCl$_2$F | H | H | OCH$_2$C≡CH |
| 24 | 3-N(CF$_3$)SCCl$_2$F | H | H | OCH$_2$CH$_2$SC$_2$H$_5$ |
| 25 | 4-N(CF$_3$)SCCl$_2$F | H | H | OCH$_2$CCl$_3$ |
| 26 | 4-N(CF$_3$)SCCl$_2$F | H | H | O(CH$_2$)$_{11}$CH$_3$ |
| 27 | 4-N(CF$_3$)SCCl$_2$F | H | H | OCH$_2$CH$_2$OCH$_3$ |
| 28 | 4-N(CF$_3$)SCCl$_2$F | H | H | OCH$_2$CH═CH$_2$ |
| 29 | 4-N(CF$_3$)SCCl$_2$F | H | H | OCH$_2$—C≡CH |
| 30 | 4-N(CF$_3$)SCCl$_2$F | H | H | NHCH$_2$CH$_2$CH$_2$OCH$_3$ |
| 31 | 4-N(CF$_3$)SCCl$_2$F | H | H | OCH$_2$CH$_2$OCH$_2$CH$_2$OCH$_3$ |
| 32 | 4-N(CF$_3$)SCCl$_2$F | H | H | N(CH$_3$)CH$_2$CH$_2$CN |
| 33 | 3-N(CF$_3$)SCCl$_2$F | 4-Cl | H | OCH$_3$ |
| 34 | 3-N(CF$_3$)SCCl$_2$F | 4-Cl | H | OC$_3$H$_7$i |
| 35 | 4-N(CF$_3$)SCCl$_2$F | H | H | —O—⌬—COOCH$_3$ (ortho) |
| 36 | 4-N(CF$_3$)SCCl$_2$F | H | H | —O—⌬ |

TABLE 1-continued

| Extender No. | —N(CF$_3$)SCCX$_3$ | Y$^1$ | Y$^2$ | Z |
|---|---|---|---|---|
| 37 | 3-N(CF$_3$)SCCl$_2$F | H | H | " |
| 38 | 4-N(CF$_3$)SCCl$_2$F | H | H | —O—⟨C$_6$H$_4$⟩—Cl |
| 39 | 3-N(CF$_3$)SCCl$_2$F | 6-Cl | H | O½ Zm$^{2+}$ |

Extender Nos. 2, 4, 5, 6, 13, 14, 19 and 25 are particularly preferred.

The new mixtures of the active compounds and the extenders can be employed against a large number of nematodes and insects, typical soil pests being the focus, but it also being possible to affect all the other important arthropods which usually occur, or occur only purely accidentally at times, in the soil or close to the soil.

From the order of the Isopoda, for example, *Oniscus asellus, Armadillidium vulgare* and *Porcellio scaber*. From the order of the Diplopoda, for example, *Blaniulus guttulatus*. From the order of the Chilopods, for example, *Geophilus carpophagus* and *Scutigera* spec. From the order of the Symphyla, for example, *Scutigerella immaculata*. From the order of the Thysanura, for example *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria*. From the order of the Dermaptera, for example, *Forficula auricularia*. From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudopretella, Cacoecia podana, Capua reticulana, Choristoneura fumiferana, Clysia ambiguella, Homona magnanima* and *Tortrix viridana*. From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica*. From the order of the Hymenoptera, for example, Diprion spp., Hoplocampa spp., Lasium spp., *Monomorium pharaonis* and Vespa spp. From the order of the Diptera, for example, Aedes spp., Anopheles spp., Culux spp., *Drosophila melanogaster,* Musca spp., Fannia spp., *Calliphora erythrocephala,* Lucilia spp., Chrysomyia spp., Cuterebra ssp., Gastrophilus spp., Hypobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa*. From the order of the Siphonaptera, for example, *Xenopsylla cheopis* and Ceratophyllus spp.

The phytoparasitic nematodes include, for example, Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp.

The new agents for combating pests are particularly preferably employed against the abovementioned nematodes. Moreover, they are preferably employed against pests from the group of the "corn rootworms" of the genera Diabrotica, such as *Diabrotica virgifera, Diabrotica balteata* and *Diabrotica longicornis*.

The mixtures of active compounds and extenders can be converted to the customary formulations, such as solutions, emulsions, suspensions, powders, granules, natural and synthetic materials impregnated with active compound and very fine capsules in polymeric substances and in coating compositions for seed.

These formulations are produced in known manner, for example by mixing the active compounds with extenders, that is, liquid solvents and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as diemthylformamide and dimethylsulphoxide, as well as water.

As solid carriers there are suitable: for example ground natural minerals, such as kaolins, clays, talc, chalk, quartz, attapulgite, montmorillonite or diatomaceous earth, and ground synthetic minearals, such as highly dispersed silicic acid, alumina and silicates; as solid carriers for granules there are suitable: for example crushed and fractionated natural rocks, such as calcite, marble, pumice, sepiolite, dolomite and brick gravel, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins, and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Preferred formulation forms are granules, emulsifiable concentrates, suspension concentrates and water-dispersible powders.

The formulations in general contain between 0.1 and 95 percent by weight of the mixture of active compound and extender, preferably between 0.5 and 90%.

It is also possible to formulate the active compounds and extenders separately and to mix the formulated products, or to apply the formulated products separately in their formulations.

The mixtures according to the invention can be present in their commercially available formulations and in the use forms, prepared from these formulations, as a mixture with other active compounds, such as other insecticides, baits, sterilizing agents, acaricides, nematicides, fungicides or growth-regulating substances. The other insecticides, include, for example, phosphates, carbamates, carboxylates, chlorinated hydrocarbons, phenylureas, pyrethroids, substances produced by microorganisms, and others.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The mixtures are employed in a customary manner appropriate for the use forms. As already indicated above, it is also possible to use the active compounds and extenders in (optionally different) separate formulations in mixtures of the formulations or as separate formulations.

The active compound content of the use forms prepared from the commercially available formulations can vary within wide limits. The active compound concentration of the use forms can be from 0.0000001 to 95% by weight of active compound, preferably between 0.0001 and 20% by weight.

The proportions of active compound to extender in the formulations can vary within wide limits, depending on the chosen extender and the relative activity of the particular active compound used and the active compound content in the formulation, without the prolonging in action being lost. The ratios (weight ratios) of active compounds/extender are preferably between the ranges of 1:50 and 50:1, particularly preferably between 1:20 and 20:1 and very particularly preferably between 1:10 and 10.1

The new mixtures of active compounds and extenders and preferably employed in amounts of between 0.1 and 10 kg/ha, preferably between 0.5 and 5 kg/ha, and particularly preferably between 0.8 and 2 kg/ha (based on the non-formulated substances).

The expert can easily determine the most advantageous formulations, compositions and use amounts for solving the particular problems with the aid of his expert knowledge or with the aid of simple orientating experiments.

The preparation of the new sulphenic acid amides according to the invention will be illustrated with the aid of the following examples:

(I) Preparation of the salts (Z denotes OM)

EXAMPLE I/1

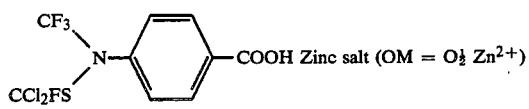COOH Zinc salt (OM = O½ Zn$^{2+}$)

A solution of 17 g (1/20 mole) of 4-N-trifluoromethyl-N-(dichlorofluoromethylthio)-aminobenzoic acid in 50 ml of methanol is added to a solution of 4.2 g (1/20 mole) of sodium bicarbonate in 50 ml of water. A vacuum is briefly applied to this aqueous-methanolic solution to remove the $CO_2$ formed, and a solution of 3.5 g (1/40 mole) of zinc chloride in 150 ml of water is then added dropwise. The zinc salt thereby precipitates immediately. The product is filtered off with suction and dried at 70°. Yield: 18 g; melting point: 252°–56° C.

The following salts are obtained in an analogous manner:

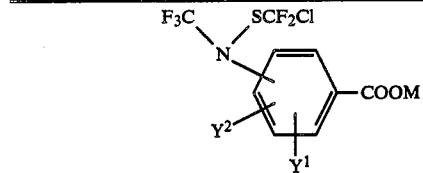

| Example No. | Position of N(CF$_3$)SCF$_2$Cl | Y$^1$ | Y$^2$ | M | M.p. (°C.) |
|---|---|---|---|---|---|
| I/2 | 4 | H | H | ½ Cu$^{2+}$ | 260–262 |
| I/3 | 4 | H | H | ½ Mg$^{2+}$ | 110 (decomposition) |
| I/4 | 3 | H | H | ½ Zn$^{2+}$ | 80 |
| I/5 | 3 | H | H | ½ Cu$^{2+}$ | 206 |
| I/6 | 2 | H | H | ½ Zn$^{2+}$ | 80 |
| I/7 | 3 | 4-Cl | H | ½ Zn$^{2+}$ | 175–178 |
| I/8 | 3 | 4-Cl | H | ½ Cu$^{2+}$ | 170 |

II Preparation of the esters (Z denotes OR$^1$)

Example II/1

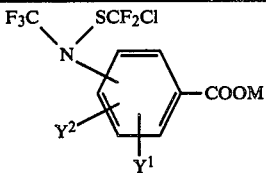

1060 g (3.1 moles) of 3-N-(fluorodichloromethylthio)-N-(trifluoromethyl)-aminobenzoyl fluoride and 145 g (3.15 moles) of ethanol are dissolved in 3 liters of toluene, and 345 g (3.4 moles) of triethylamine are added at 20°–30° C., with cooling. The reaction mixture is stirred for about 1 hour, washed 3 times with 1 liters of water each time and dried over sodium sulphate and the solvent is distilled off in vacuo. The residue (1275 g) is then distilled in vacuo. 1058 g=82% of theory of boiling point$_{0.4}$ mm Hg, 122°–24° C. are obtained.

The compounds of the following examples are obtained in the same manner:

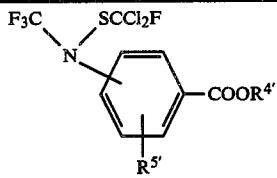

| Example No. | Position of N(CF$_3$)SCCl$_2$F | R$^{5'}$ | R$^{4'}$ | B.p. (°C.) mm Hg (n$_b^{20}$) |
|---|---|---|---|---|
| II/2 | 3 | H | CH$_3$ | 115°/0.3 |
| II/3 | 4 | H | CH$_3$ | 120°/0.3 |
| II/4 | 2 | H | CH$_3$ | 120°/0.3 |
| II/5 | 4 | H | C$_4$H$_9$n | 125°/0.2 |
| II/6 | 3 | H | C$_4$H$_9$n | 140°/0.3 |
| II/7 | 2 | H | C$_4$H$_9$n | 170°/0.3 |
| II/8 | 2 | H | CH$_2$CH$_2$Cl | 125°/0.1 |
| II/9 | 2 | H | CH$_2$CCl$_3$ | 138–40°/0.1 |
| II/10 | 2 | H | C$_{12}$H$_{25}$ | 179–80°/0.1 |
| II/11 | 2 | H | CH$_2$CH$_2$OCH$_3$ | 125–130°/0.1 |
| II/12 | 2 | H | CH$_2$CH=CH$_2$ | 110–12°/0.1 |
| II/13 | 2 | H | CH$_2$C≡CH | 112–15°/0.1 |
| II/14 | 2 | H | CH$_2$CH$_2$SC$_2$H$_5$ | 145–50°/0.1 |
| II/15 | 2 | H | C$_{16}$H$_{33}$ | 215–20°/0.08 |
| II/16 | 2 | H | CH$_2$CH$_2$OCH$_2$CH$_2$OCH$_3$ | 160–63°/0.08 |
| II/17 | 3 | H | CH$_2$CH$_2$Cl | 125–30°/0.08 |
| II/18 | 3 | H | CH$_2$CCl$_3$ | 140–45°/0.1 |
| II/19 | 3 | H | C$_{12}$H$_{25}$ | 185–90°/0.07 |
| II/20 | 3 | H | CH$_2$CH$_2$OCH$_3$ | 126–30°/0.1 |
| II/21 | 3 | H | CH$_2$CH=CH$_2$ | 120–25°/0.1 |
| II/22 | 3 | H | CH$_2$C≡CH | 123–27°/0.1 |
| II/23 | 3 | H | CH$_2$CH$_2$SC$_2$H$_5$ | 150–53°/0.1 |

-continued

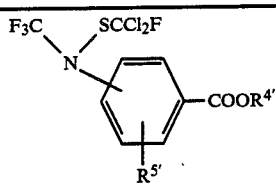

| Example No. | Position of N(CF3)SCCl2F | R5' | R4' | B.p. (°C.) mm Hg (n_b^{20}) |
|---|---|---|---|---|
| II/24 | 3 | H | CH2CH2OCH3 | (1.5164) |
| II/25 | 3 | H | CH2CH2CH2OCH3 | (1.5136) |
| II/26 | 3 | H | CH2CH2OCH2CH2OCH3 | 154–60°/0.08 |
| II/27 | 4 | H | CH2CH2Cl | 130–35°/0.1 |
| II/28 | 4 | H | CH2CCl3 | 140–45°/0.08 |
| II/29 | 4 | H | C12H25 | 195°/0.08 |
| II/30 | 4 | H | CH2CH2OCH3 | 130–35°/0.1 |
| II/31 | 4 | H | CH2CH=CH2 | 120–25°/0.1 |
| II/32 | 4 | H | CH2C≡CH | 125–30°/0.1 |
| II/33 | 4 | H | CH2CH2OC2H5 | 160–65°/0.12 |
| II/34 | 4 | H | CH2CH2OCH2CH2OCH3 | 163–68°/0.08 |
| II/35 | 3 | 4-Cl | C2H5 | (1.5089) |
| II/36 | 3 | 4-Cl | CH3 | (1.5153) |
| II/37 | 3 | 4-Cl | C3H7i | (1.5031) |
| II/38 | 3 | 4-Cl | C12H25 | (1.4867) |

The prolonged duration of action of the new mixtures according to the invention may be illustrated by the following examples.

In order rapidly to achieve advantageous results in the discovery and development of suitable extenders under laboratory and greenhouse conditions, model soils suitable for the investigations are developed and the tests were carried out at relatively high soil temperatures of 20°–25° C.

The active compounds employed in Examples A and B can be illustrated by the following formulae:

1. 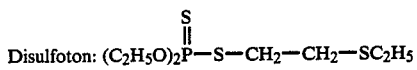
Disulfoton: (C2H5O)2P(=S)—S—CH2—CH2—SC2H5

2. 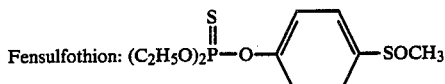
Fensulfothion: (C2H5O)2P(=S)—O—⟨phenyl⟩—SOCH3

3. 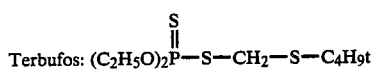
Terbufos: (C2H5O)2P(=S)—S—CH2—S—C4H9t

4. 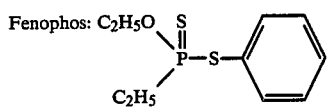
Fenophos: C2H5O, C2H5 P(=S)—S—⟨phenyl⟩

5. 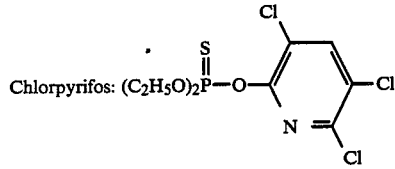
Chlorpyrifos: (C2H5O)2P(=S)—O—⟨trichloropyridyl⟩

6. 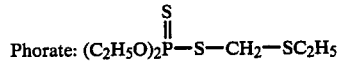
Phorate: (C2H5O)2P(=S)—S—CH2—SC2H5

7. Phoxim: (C2H5O)2P(=S)—O—N=C(CN)(C6H5)

8. 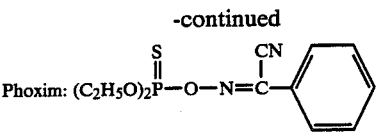
Carbofuran:

9. 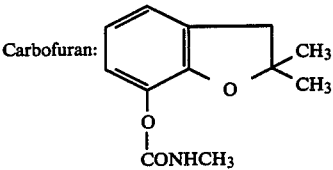
Isofenphos

10. 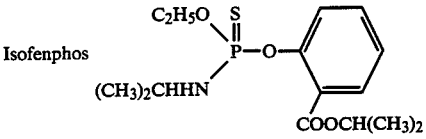
Fenamiphos (CH3)2CH—P(=O)(OC2H5)—O—⟨tolyl-SCH3⟩

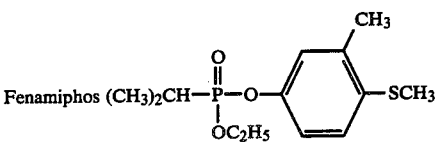

EXAMPLE A

1. Model soil used

Composition (percent by weight):
60% of garden soil
30% of sand
10% of peat

2. Experimental procedure and results

For the investigations, in each case 4 mg of active compound by itself or a mixture of in each case 4 mg of active compound and 4 mg of the extenders listed were mixed with in each case 1 l of the model soil, so that the individual substances were in each case present in concentrations of 4 ppm. After storage of the soils thus pretreated, after 1 week ½ l of soil and after 4 weeks the remaining half l were infested with 20 seven day-old larvae of *Diabrotica balteata*. On the day of infestation pre-swollen corn seeds were places on the bottom of each container so that, upon germination into seedlings, they served as food for the larvae.

In each case 6 days after the infestation with the test larvae, the degree of action of the active compound by itself and of the mixture of active compound and extender were determined in % by counting the dead and living larvae. The degree of action is 100% if all the test larvae have been destroyed, and is 0% if just as many test larvae survive as in the case of the untreated control.

The active compound, extender, amounts applied and results can be seen from the following tables:

| Example A1 Active Compound: carbofuran | | | |
|---|---|---|---|
| Active compound concentration in ppm | Extender No. 1 (see Table 1 above) Concentration in ppm | % Destruction of the Diabrotica larvae after | |
| | | 1 week | 4 weeks |
| Carbofurant: | | | |
| 4 | 0 | 100 | 0 |
| 10 | 0 | 100 | 0 |
| 0 | 10 | 0 | 0 |
| 0 | 30 | 0 | 0 |
| 4 | 4 | 100 | 100 |

| Example A2 Active compound: isohpenphos | | | |
|---|---|---|---|
| Active compound concentration in ppm | Each of Extenders Nos. 1–38 (see Table 1 above) Concentration in ppm | % Destruction of the Diabrotic larvae after | |
| | | 1 week | 4 weeks |
| Isophenphos: | | | |
| 4 | 0 | 100 | 0 |
| 10 | 0 | 100 | 0 |
| 0 | 10 | 0 | 0 |
| 4 | 4 | 100 | 100 |

The extenders by themselves had no destructive action in the concentrations used.

The foregoing experiments, which involved illustrative concentrations, show that the mixtures of active compounds and extenders exhibit high activity significantly longer than the active compounds themselves.

EXAMPLE B

1. Model soil used

Composition (percent by weight):
90% of sand soil
10% of peat

2. Experimental procedure and results

For the investigations, in each case 4 mg of active compound by itself or a mixture of in each case 4 mg of active compound and 10 mg of the extenders listed were mixed with in each case 1 l of the model soil, so that the individual substances were in each case present in concentrations of 4 or 10 ppm. After storage of the soils thus pretreated, after 1 week ½ l of soil and after 4 weeks the remaining half liter were infested with 10 seven day-old larvae of *Diabrotica balteata*. On the day of infestation pre-swollen corn seeds were placed on the bottom of each container so that, upon germination into seedlings, they served as food for the larvae.

In each case 6 days after infestation with the test larvae, the degree of action of the active compound by itself and of the mixture of active compound and extender was determined in % by counting the dead and living larvae. The degree of action is 100% if all the test larvae have been destroyed, and is 0% if just as many test larvae are still alive as in the case of the untreated control.

The active compound, extenders, amounts applied and results can be seen from the following tables:

Active compounds employed in Example B:
1. Disulfoton
2. Fensulfothion
3. Terbufos
4. Fenophos
5. Chlorpyrifos
6. Phorate
7. Phoxim
8. Carbofuran
9. Isofenphos

| Each of Active compounds 1–9, concentration in ppm | Each of Extenders Nos. 1–38 (compare Table 1 above) Concentration in ppm | % destruction of the Diabotica larvae after | |
|---|---|---|---|
| | | 1 week | 4 weeks |
| 4 | 0 | 100 | 0 |
| 4 | 10 | 100 | 100 |

The experiments with concentrations prepared purely as examples show that the mixtures of active compounds and extenders have a (high) action which is several times longer than that of the active compounds by themselves.

The foregoing experiments, which involved illustrative concentrations, show that the mixtures of active compounds and extenders exhibit high activity significantly longer than the active compounds themselves.

EXAMPLE C

Model soil and test procedure correspond to Example A. However, *Musca domestica* larvae were used as test larvae and the degree of action was determined after 2 and 6 weeks. Fenamiphos was used as active ingredient (active compound 10).

| Active compound concentration in ppm | Extender No. (compare Table 1 above) Concentration in ppm | % destruction of the Musca larvae after | |
|---|---|---|---|
| | | 2 weeks | 6 weeks |
| Active compound 10–4 ppm | 0 ppm | 100 | 0 |
| Active compound 10–4 ppm | Extender No. 1 4 ppm | 100 | 100 |

It will be understood that the specification and examples are illustrative but not limitative of the present invention and that other embodiments within the spirit and scope of the invention will suggest themselves to those skilled in the art.

We claim:

1. A nematicidal or insecticidal composition comprising a nematicidally or insecticidally effective amount of a known nematode or insecticide and a duration prolonging effective amount of a sulphenic acid amide of the formula

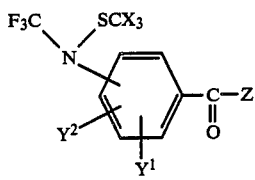

in which
X each independently is fluoroine or chlorine,
$Y^1$ and $Y^2$ each independently is hydrogen, halogen, alkyl, alkoxy, halogenalkyl or $NO_2$,
Z is $-OR^1$ or $-OM$,
$R^1$ is alkyl, alkenyl or alkinyl optionally substituted by halogen, cyano, alkoxy, alkylthio or alkoxyalkoxy, and
M is ammonium or one equivalent of an alkali metal, alkaline earth metal or copper, zinc, manganese, nickel or iron cation.

2. A composition according to claim 1, wherein the nematicide or insecticide is a P ester, carbamate or pyrethroid.

3. A composition according to claim 1, wherein the nematicide or insecticide is a carbamate or a phosphoric or phosphonic acid ester, ester-amide or a thiono, thiol or thiono-thiol counterpart thereof.

4. A composition according to claim 1 in which
X each independently is fluorine or chlorine,
$Y^1$ and $Y^2$ each independently is hydrogen, halogen, alkyl, alkoxy, halogenalkyl or $NO_2$,
Z is $-OM$, and
M is copper or zinc.

5. A method of combating nematodes or insects over a prolonged period of time which comprises applying to a nematode or insect habitat a nematicidally or insecticidally effective amount of a composition according to claim 1.

6. A method of combating nematodes or insects over a prolonged period of time which comprises applying to a nematode or insect habitat a nematicidally or insecticidally effective amount of a composition according to claim 4, wherein the nematicide or insecticide is a carbamate or a phosphoric or phosphonic acid ester, ester-amide or a thiono, thiol or thiono-thiol counterpart thereof.

* * * * *